United States Patent [19]

Whitney

[11] 4,348,404
[45] Sep. 7, 1982

[54] ANTIINFLAMMATORY 4,5-DIARYL-α-POLYFLUOROALKYL-1H-IMIDAZOLE-2-METHANAMINES

[75] Inventor: Joel G. Whitney, Kennett Square, Pa.

[73] Assignee: E. I. Du Pont de Nemours and Company, Wilmington, Del.

[21] Appl. No.: 271,276

[22] Filed: Jun. 15, 1981

Related U.S. Application Data

[63] Continuation-in-part of Ser. No. 170,871, Jul. 21, 1980, abandoned.

[51] Int. Cl.$^3$ .................. A61K 31/415; A61K 31/44; C07D 233/64; C07D 401/04
[52] U.S. Cl. ................................ 424/273 R; 548/342; 546/256; 546/278; 424/263
[58] Field of Search ................ 548/342; 546/256, 278; 424/263, 273 R

[56] References Cited

U.S. PATENT DOCUMENTS

| | | | |
|---|---|---|---|
| 2,532,547 | 12/1950 | Goldberg et al. | 548/342 |
| 3,197,480 | 7/1965 | England | 260/326.5 |
| 3,707,475 | 12/1972 | Lombardino | 548/342 |
| 3,929,807 | 12/1975 | Fitzi | 546/278 |
| 4,159,338 | 6/1979 | Cherkofsky et al. | 546/278 |
| 4,190,666 | 2/1980 | Cherkofsky et al. | 424/274 |
| 4,199,592 | 4/1980 | Cherkofsky | 424/273 R |

FOREIGN PATENT DOCUMENTS

5219 11/1979 European Pat. Off.
2164919 7/1973 Fed. Rep. of Germany.

*Primary Examiner*—Henry R. Jiles
*Assistant Examiner*—Natalia Harkaway

[57] ABSTRACT

Antiinflammatory 4,5-diaryl-α-polyfluoroalkyl-1H-imidazole-2-methanamines such as 4,5-bis(4-methoxyphenyl)-α,α-di(trifluoromethyl)-1H-imidazole-2-methanamine, are useful in treatment of arthritis.

27 Claims, No Drawings

ANTIINFLAMMATORY 4,5-DIARYL-α-POLYFLUOROALKYL-1H-IMIDAZOLE-2-METHANAMINES

CROSS REFERENCE TO RELATED APPLICATIONS

This is a continuation-in-part application of copending Patent Application Ser. No. 06/170,871, filed July 21, 1980, now abandoned.

BACKGROUND OF THE INVENTION

This invention relates to antiinflammatory imidazoles.

Cherkofsky et al., U.S. Pat. No. 4,190,666 discloses antiinflammatory 4,5-diaryl substituted imidazoles of the formula

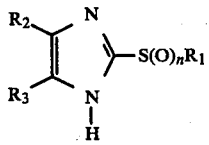

where $R_1$, $R_2$, and $R_3$ represent various defined groups, and n is an integer of 0–2.

German DS No. 2164-919 discloses imidazole-2-carbinols of the formula

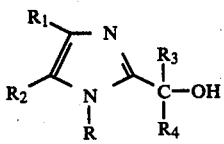

where

R, $R_1$, $R_2$, $R_3$ and $R_4$ represent various defined groups. The compounds are stated to have hypo-cholesteraemic activity and also are able to lower the triglyceride level in blood serum.

D. C. England, U.S. Pat. No. 3,197,480 includes disclosure of the compound:

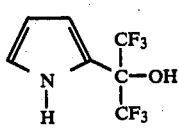

Pharmaceutical use for the compounds of this patent is not disclosed.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

In addition to antiinflammatory properties, some of the compounds of this invention have analgesic activity. This additional property is desirable in treatment of arthritis and related diseases; however, such compounds can be employed solely to alleviate pain.

SUMMARY OF THE INVENTION

This invention relates to compounds of formula I, pharmaceutical compositions containing them, and methods of use of these compounds to treat inflammation.

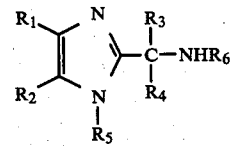

wherein $R_1$ and $R_2$ independently are 2-pyridyl, 3-pyridyl, 4-pyridyl or

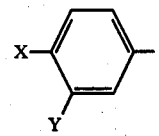

where

X=H, F, Cl, Br, $C_1$–$C_2$ alkyl, $C_1$–$C_2$ alkoxy, di($C_1$–$C_2$ alkyl)amino, ($C_1$–$C_2$ alkyl)S(O)$_n$, or $NO_2$; where n=0, 1 or 2;

Y=H, F or Cl; provided when Y=F or Cl, then X must be F or Cl;

further provided that only one of $R_1$ and $R_2$ can be selected from the group of 2-pyridyl and 4-pyridyl;

$R_3$ and $R_4$ independently=H, $CF_3$, $CF_2H$, $CF_2Cl$, $CFCl_2$ or $CF_2CF_3$; provided that no more than one of $R_3$ and $R_4$ can be H; and further provided that no more than one of $R_3$ and $R_4$ can be $CF_2CF_3$;

$R_5$ and $R_6$ independently=H or $C_1$–$C_3$ alkyl; or a pharmaceutically suitable acid addition salt thereof.

Preferred Compounds

Preferred compounds for utility considerations or ease of synthesis are those where, independently;

(a) $R_1$ and $R_2$ independently=4—$XC_6H_4$— where X=H, F, Cl, $CH_3O$ or $CH_3$; or (b) $R_3$ and $R_4$=trifluoromethyl; or (c) $R_5$=H or $CH_3$; or (d) $R_6$=H.

Most preferred compounds are those where $R_1$ and $R_2$ independently=4—$XC_6H_4$— where X=H, F, Cl, $CH_3O$ or $CH_3$;

$R_3$ and $R_4$=trifluoromethyl;

$R_5$=H or $CH_3$; and $R_6$=H.

Specifically preferred compounds are (1) 4,5-bis(4-methoxyphenyl)-α,α-di(trifluoromethyl)-1H-imidazole-2-methanamine;

(2) 4,5-bis(4-fluorophenyl)-α,α-di(trifluoromethyl)-1H-imidazole-2-methanamine; and (3) 4,5-bis(4-fluorophenyl)-1-methyl-α,α-di(trifluoromethyl)-1H-imidazole-2-methanamine.

Synthesis

Compounds of Formula I can be prepared by contacting an N-protected 4,5-diaryl imidazole with a strong base, such as butyl lithium, in an inert solvent at low temperatures, followed by reaction with an appropriate fluorinated ketone imine.

The nature of the N-protecting group is such that it is stable to strong bases. When the N-protecting group is $C_1$–$C_3$ alkyl, compounds of Formula I where $R_5 = C_1$–$C_3$ alkyl are obtained. When the N-protecting group is acid labile and removed by an acidic reagent, compounds of Formula I where $R_5 = H$ are obtained. Examples of useful acid labile protecting groups are 2-tetrahydropyranyl, benzyloxymethyl, methoxymethyl, methylthiomethyl, $\beta$-methoxyethoxymethyl, 2-tetrahydrofuranyl and $\alpha$-ethoxyethyl.

The synthesis of N-protected 4,5-disubstituted imidazoles is described in U.S. Pat. No. 4,190,666; U.S. Pat. No. 4,182,769; and U.S. Pat. No. 4,159,338.

Introduction of a fluorinated ketone imine where $R_6 = H$ requires protection of the imine nitrogen with a group which can later be removed by acid. An example of a useful group is trimethylsilyl.

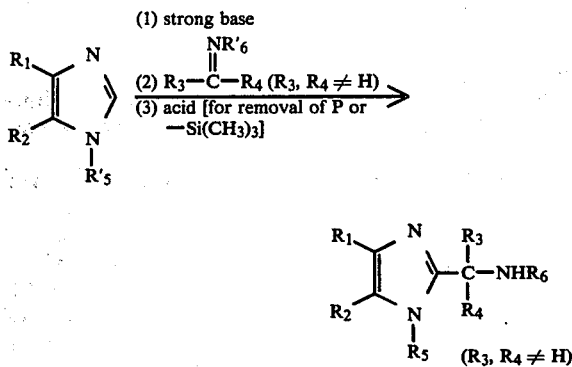

$R_5' = C_1$–$C_3$ alkyl or P (acid labile protecting group)
$R_6' = C_1$–$C_3$ alkyl or —Si(CH$_3$)$_3$ Compounds of Formula I of this invention with one of $R_3$ or $R_4 = H$ can be prepared by a two-step process from 1-(4,5-diaryl-1H-imidazol-2-yl)-polyfluoro-1-alkanones, by conversion to the oximes followed by reduction.

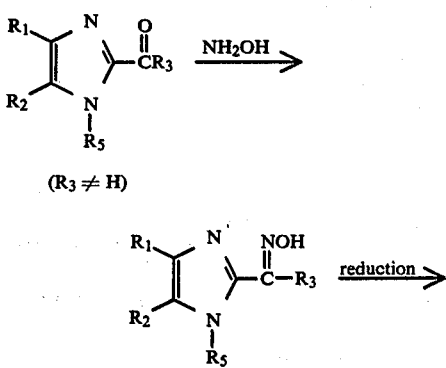

The 1-(4,5-diaryl-1H-imidazol-2-yl)-polyfluoro-1-alkanones can be prepared from the corresponding N-substituted or N-protected 4,5-diaryl-1H-imidazoles by treatment with a strong base, such as n-butyl lithium, in an inert solvent at low temperature, followed by a fluorinated acid anhydride or an N,N-disubstituted fluorinated acid amide, followed by removal of the N-protecting group if present.

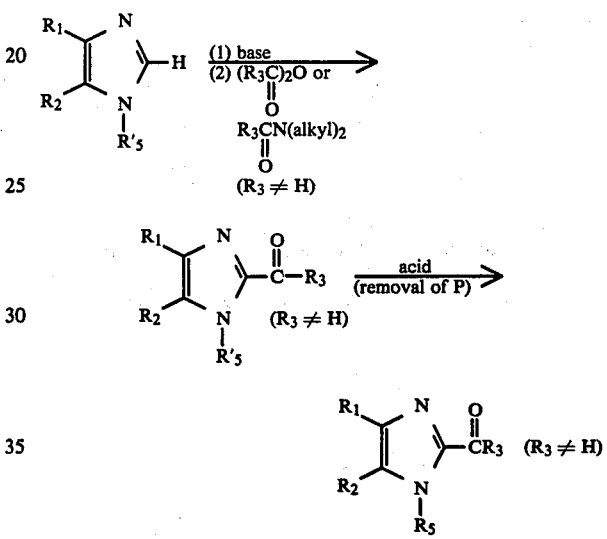

The oximes can be prepared by heating the polyfluoro-1-alkanones in the presence of hydroxylamine hydrochloride and a base (such as an alkali metal acetate, alkoxide, hydroxide or carbonate) in a polar solvent such as ethanol.

The reduction of the oxime is carried out by catalytic-hydrogenation or by metal hydride reduction. Preferred conditions involve the use of lithium aluminum hydride in an ether solvent, such as diethyl ether or tetrahydrofuran at room temperature to the boiling point of the solvent.

A smilar procedure used in the preparation of 1-phenyl-2,2,2-trifluoroethylamine hydrochloride has been described in the literature [R. A. Shepard and S. E. Wentworth, J. Org. Chem., 32, 3197 (1967)].

Compounds of Formula I of this invention with $R_5$ and/or $R_6 = C_1$–$C_3$ alkyl can be prepared by alkylation of the corresponding compounds with $R_5$ and/or $R_6 = H$. Alkylation can occur on either or both of the NH$_2$ or NH functionalities, depending on the conditions of the reaction. Often mixtures of alkylated products are obtained which can be separated by conventional techniques. These alkylations can be conducted in the presence of a base, such as potassium carbonate, pyridine, triethylamine, potassium t-butoxide, sodium hydride or the like. An example of an alkylating agent is methyl iodide.

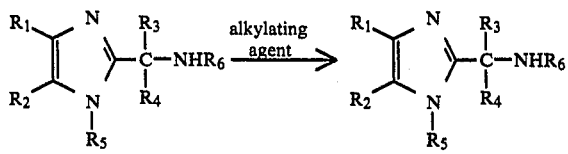

($R_5$ and/or $R_6$ = H)

Pharmaceutically suitable salts of the compounds of Formula I can be prepared by treatment of the free base I with an appropriate acid.

In the following examples, all parts are by weight and temperatures are in degrees centigrade unless otherwise specified.

EXAMPLE 1

4,5-Bis(4-methoxyphenyl)-α,α-di(trifluoromethyl)-1H-imidazole-2-methanamine

A solution of 10.0 g (28.4 mmoles) of 1-(α-ethoxyethyl)-4,5-bis-(4-methoxyphenyl)-1H-imidazole and 3.9 g of tetramethylethylenediamine in 150 ml THF was cooled to −78° C. with a dry-ice acetone bath, and a solution of 30 ml of of 1.6 M butyl lithium in hexane was then added dropwise. After stirring for 15 minutes, 11.5 g (48.5 mmoles) of [1,1-di(trifluoromethyl)methyleneamino]trimethylsilane [R. F. Swindell et al., Inorganic Chemistry, 11, #2, 242 (1972)] was added dropwise, and the reaction mixture was then allowed to warm to room temperature. A solution of 10% aqueous sodium bicarbonate (100 ml) was added dropwise and the organic layer was separated and concentrated in vacuo. The residue was stirred with a mixture of 200 ml of ethanol and 100 ml 2 M aqueous HCl overnight. The ethanol was evaporated under vacuum and the aqueous phase was extracted with ether. The combined ether extracts were washed with water, dried and concentrated to give 4.6 g (36%) of crude 4,5-bis(4-methoxyphenyl-α,α-di(trifluoromethyl)-1H-imidazole-2-methanamine. The residue was chromatographed on silica gel eluting with chloroform to give, after recrystallization from methylcyclohexane, the product as colorless crystals, m.p. 127°–128.5° C.

Anal. Calcd. for $C_{20}H_{17}F_6N_3O_2$: C, 53.93; H, 3.82; N, 9.44. Found: C, 53.95, 54.0, 54.1; H, 3.92, 3.81, 3.80; N, 9.44, 9.28, 9.20.

EXAMPLE 2

4,5-Bis(4-fluorophenyl)-α-trifluoromethyl-1H-imidazole-2-methanamine

A.

1-[4,5-Bis(4-fluorophenyl)-1H-imidazol-2-yl]-2,2,2-trifluoro-1-ethanone

To a cooled (−78°) suspension of 5.0 g (14.7 mmoles) of 4,5-bis(4-fluorophenyl)-1-(2-tetrahydropyranyl)-1H-imidazole in 75 ml of ether containing 1.9 g (16.4 mmoles) of tetramethylethylenediamine was added dropwise 18.0 ml (28.8 mmoles of a 1.6 M solution of n-butyl lithium solution. After stirring at −78° for 10 minutes, a solution of 6.1 g (29 mmoles) of trifluoroacetic anhydride in 25 ml of ether was added dropwise. The reaction mixture was allowed to warm to room temperature and then washed with 10% aqueous sodium bicarbonate solution. The ether layer was dried and evaporated. The oily residue was purified by chromatography on silica gel using toluene as the eluent to give 1.65 g of 1-(4,5-bis(4-fluorophenyl)-1-(2-tetrahydropyranyl)-1H-imidazol-2-yl]-2,2,2-trifluoro-1-ethanone as a semicrystalline colorless oil.

The intermediate product was stirred with a mixture of 20 ml of ethanol and 10 ml of 1 N hydrochloric acid at room temperature overnight. The reaction mixture was poured onto water and the product extracted into ether. The combined organic extracts were washed with water, dried and concentrated under vacuum. The residual oil was purified by chromatography on silica gel using chloroform or toluene as the eluent. The product fraction was crystallized from toluene/hexane (1:4) to give 700 mg of the title compound as colorless crystals, m.p. 214°–215.5°. The proton and fluorine NMR spectra were consistent with the assigned structure.

Anal. Calcd. for $C_{17}H_9F_5N_2O$: C, 57.95; H, 2.56; N, 7.95. Found: C, 58.31; 58.26; H, 2.77; 2.77; N, 7.84; 7.84.

B.

1-[4,5-Bis(4-fluorophenyl)-1H-imidazol-2-yl]-2,2,2-trifluoro-1-ethanone, Oxime

To a solution of the above ketone (5.28 g, 0.015 mole) in 100 ml of ethanol, a solution of hydroxylamine (2.07 g of hydroxylamine hydrochloride, and 1.62 g of sodium methoxide in 10–15 ml of water) was added. The mixture was heated to reflux for 24 hours. The reaction mixture was cooled, and another aliquot of hydroxylamine added, and refluxed for another period of 24 hours. This process was repeated a third time. After this 72-hour reaction time was over, the reaction mixture was cooled, diluted with 400 ml of water, the precipitated solids collected by filtration, and purified by column chromatography, using chloroform and ethanol (90/10). Yield of purified oxime 3 g (57%), which melted at 235°. The mass spectral analysis and N.M.R. data were in agreement with the assigned structure.

Anal. Calcd. for $C_{17}H_{10}F_5N_3O$: C, 55.59; H, 2.74; N, 11.44. Found: C, 55.9, 55.8; H, 3.0, 2.9; N, 11.5, 11.7.

C.

4,5-Bis(4-fluorophenyl)-α-trifluoromethyl-1H-imidazole-2-methanamine

The oxime described above (3.00 g, 0.0085 mole) was dissolved in anhydrous tetrahydrofuran (60 ml) and added dropwise to a solution of lithium aluminum hydride (1.1 g) in 30 ml of tetrahydrofuran. The reaction mixture was refluxed for 18 hours. Excess reducing agent was destroyed by the addition of ethyl acetate and then a saturated solution of sodium bicarbonate (20 ml) was added, and the mixture heated on a steam bath. Inorganic salts were filtered off, and the filter washed with tetrahydrofuran. The solvent was then evaporated under vacuo. The crude residue was then dissolved in methylene chloride, washed with water, then the solvent was removed under vacuo to yield a dark-brown oil. The crude product was then chromatographed on a silica gel column (250 g silica gel), using toluene and ethyl acetate (90/10) as eluant mixture to remove faster-moving side products. The desired compound was obtained with 100% ethyl acetate as the eluant to yield 1.2 g (35%); the product melted at 188°–191°. The NMR and mass spectral data were in agreement with the structure assigned above.

Anal. Calcd. for $C_{17}H_{12}F_5N_3$: C, 57.79; H, 3.42; N, 11.89. Found: C, 57.8; H, 3.6; N, 11.9.

EXAMPLE 3

4,5-Bis-(4-fluorophenyl)-N,1-dimethyl-α,α-di(trifluoromethyl)-1H-imidazole-2-methanamine To a mixture of 2.0 g of 4,5-bis(4-fluorophenyl)-1-methyl-α,α-di(trifluoromethyl)-1H-imidazole-2-methanamine and 30 ml of tetrahydrofuran cooled at −78° C. was added dropwise 4.4 ml of 1.6 M butyl lithium in hexane followed by a solution of 1.3 g of methyl iodide in 5 ml of tetrahydrofuran. The reaction mixture was stirred at −78° C. for 1 hour and then allowed to warm to room temperature. A saturated aqueous solution of sodium bicarbonate was added and the product was extracted into ether. The combined ether extracts were evaporated in vacuo to give 2.16 g of yellow solid, m.p. 169°–172°. Some purification was accomplished by chromatography on silica gel (toluene) followed by HPLC (73% hexane/25% toluene/2% acetic acid) to afford 1.0 g (49%) of 4,5-bis(4-fluorophenyl)-N,1-dimethyl-α,α-di(trifluoromethyl)-1H-imidazole-2-methanamine.

Mass Calcd.: 449. Found: 449.

Following the procedures described, the following 4,5-diaryl-α-polylfuoroalkyl-1H-imidazole-2-methanamines can be prepared.

with pharmaceuticals; either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.05 to 40 milligrams per kilogram of body weight. Ordinarily 0.1 to 20, and preferably 0.2 to 10 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stea-

TABLE I

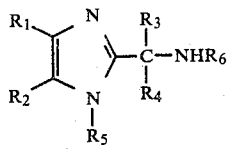

| Example | $R_1$ | $R_2$ | $R_3$ | $R_4$ | $R_5$ | $R_6$ | m.p. °C. | yield (%) |
|---|---|---|---|---|---|---|---|---|
| 1 | 4-$CH_3OC_6H_4$ | 4-$CH_3OC_6H_4$ | $CF_3$ | $CF_3$ | H | H | 127–128.5 | 36 |
| 2 | 4-$FC_6H_4$ | 4-$FC_6H_4$ | $CF_3$ | H | H | H | 188–191 | 35 |
| 3 | 4-$FC_6H_4$ | 4-$FC_6H_4$ | $CF_3$ | $CF_3$ | $CH_3$ | $CH_3$ | 169–172 | 49 |
| 4 | 4-$FC_6H_4$ | 4-$FC_6H_4$ | $CF_3$ | $CF_3$ | H | H | 153–155 | 40 |
| 5 | 4-$CH_3OC_6H_4$ | 4-$CH_3OC_6H_4$ | $CF_3$ | $CF_3$ | $CH_3$ | H | 152–153 | 69 |
| 6 | 4-$FC_6H_4$ | 4-$FC_6H_4$ | $CF_3$ | $CF_3$ | $CH_3$ | H | 138–140 | 65 |
| 7 | 4-$CH_3C_6H_4$ | 4-$CH_3C_6H_4$ | $CF_3$ | $CF_3$ | H | H | 135–136 | 43 |
| 8 | 4-$ClC_6H_4$ | 4-$ClC_6H_4$ | $CF_3$ | $CF_3$ | H | H | 145–147 | 45 |
| 9 | $C_6H_5$ | $C_6H_5$ | $CF_3$ | $CF_3$ | H | H | 127–130 | 25 |
| 10 | 4-$CH_3OC_6H_4$ | 4-$CH_3OC_5H_4$ | $CF_3$ | H | H | H | 152–154 | 31 |
| 11 | 4-$FC_6H_4$ | 4-$(CH_3)_2NC_6H_4$ | $CF_3$ | $CF_3$ | H | H | | |
| 12 | 4-$FC_6H_4$ | 4-$CH_3SC_6H_4$ | $CF_3$ | $CF_3$ | H | H | | |
| 13 | 4-$FC_6H_4$ | 4-$BrC_6H_4$ | $CF_3$ | $CF_3$ | H | H | | |
| 14 | $C_6H_5$ | 3,4-$Cl_2C_6H_3$ | $CF_3$ | $CF_3$ | H | H | | |
| 15 | 4-$FC_6H_4$ | 3-pyridyl | $CF_3$ | $CF_3$ | H | H | | |
| 16 | $C_6H_5$ | 2-pyridyl | $CF_3$ | $CF_3$ | H | H | | |
| 17 | $C_6H_5$ | 4-pyridyl | $CF_3$ | $CF_3$ | H | H | | |
| 18 | 4-$FC_6H_4$ | 4-$C_2H_5C_6H_4$ | $CF_3$ | $CF_3$ | H | H | | |
| 19 | 4-$C_2H_5OC_6H_4$ | 4-$C_2H_5OC_6H_4$ | $CF_3$ | $CF_3$ | H | H | | |
| 20 | 4-$FC_6H_4$ | 4-$(C_2H_5)_2NC_6H_4$ | $CF_3$ | $CF_3$ | H | H | | |
| 21 | 4-$FC_6H_4$ | 4-$C_2H_5SO_2C_6H_4$ | $CF_3$ | $CF_3$ | H | H | | |
| 22 | 4-$FC_6H_4$ | 4-$NO_2C_6H_4$ | $CF_3$ | $CF_3$ | H | H | | |
| 23 | 4-$FC_6H_4$ | 4-$FC_6H_4$ | $CF_3$ | $CF_2H$ | H | H | | |
| 24 | 4-$FC_6H_4$ | 4-$FC_6H_4$ | $CF_3$ | $CF_2Cl$ | H | H | | |
| 25 | 4-$FC_6H_4$ | 4-$FC_6H_4$ | $CF_3$ | $CFCl_2$ | H | H | | |
| 26 | 4-$FC_6H_4$ | 4-$FC_6H_4$ | $CF_3$ | $CF_3CF_2$ | H | H | | |
| 27 | 4-$FC_6H_4$ | 4-$FC_6H_4$ | $CF_3CF_2$ | H | H | H | | |
| 28 | 4-$FC_6H_4$ | 4-$FC_6H_4$ | $CF_3$ | $CF_3$ | n-$C_3H_7$ | H | | |
| 29 | 4-$FC_6H_4$ | 4-$FC_6H_4$ | $CF_3$ | $CF_3$ | H | n-$C_3H_7$ | | |

Dosage Forms

The antiarthritic agents of this invention can be administered to treat arthritis by any means that produces contact of the active agent with the agent's site of action in the body of a mammal. They can be administered by any conventional means available for use in conjunction ric acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in Remington's Pharmaceutical Sciences, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient 175 milligrams of lactose, 24 milligrams of talc, and 6 milligrams magnesium stearate.

A mixture of the active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in water with 0.75% sodium carboxymethylcellulose, 0.04% polysorbate 80, 0.9% benzyl alcohol, and 1.8% sodium chloride. The preparation is made sterile by autoclaving or other suitable techniques.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Use

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2, 1973, "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* is mineral oil (adjuvant) has been used extensively for the screening of drugs of potential use in rheumatoid arthritis."

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing 175-220 grams were injected subcutaneously with 0.1 ml of adjuvant in the plantar area of the right hind paw. The adjuvant was prepared by bead-milling, heat-killed, lyophilized *Mycobacterium butyricum* (Difco #0640) in light mineral oil (Fisher Scientific Co. #0-119 Paraffin Oil—Saybolt Viscosity 125/135) 5 mg/ml. Twenty non-arthritic control rats were injected with mineral oil. The animals received water and Wayne Lab-Blox ad libitum*

*while on a 10-hour light-14 hour-dark cycle

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean pawl volumes with equal standard deviation. Non-arthritic (oil-injected) control rats were distributed to 2 groups of 10. Suspensions of test compounds were prepared for dosing by bead-milling (4 mm glass beads in rubber stoppered serum bottles) for 4-5 hours in aqueous 1% polyvinyl alcohol, 5% gum acacia and 0.5% methylparaben.

Test compounds were given orally by gavage once daily for 7 days (days 14-20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the percent decrease were plotted on semi-log paper and the $ED_{50}$ percent for decrease from control paw volume was estimated by inspection.

TABLE II
Results

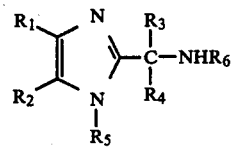

| Example | $R_1$ | $R_2$ | $R_3$ | $R_4$ | $R_5$ | $R_6$ | Adjuvant Arthritis $ED_{50}$ (mg/kg) |
|---|---|---|---|---|---|---|---|
| 1 | 4-$CH_3OC_6H_4$ | 4-$CH_3OC_6H_5$ | $CF_3$ | $CF_3$ | H | H | 2.0 |
| 2 | 4-$FC_6H_4$ | 4-$FC_6H_4$ | $CF_3$ | H | H | H | 19.0 |
| 3 | 4-$FC_6H_4$ | 4-$FC_6H_4$ | $CF_3$ | $CF_3$ | $CH_3$ | $CH_3$ | (−41% @ 25)[1] |
| 4 | 4-$FC_6H_4$ | 4-$FC_6H_4$ | $CF_3$ | $CF_3$ | H | H | 1.7 |
| 5 | 4-$CH_3OC_6H_4$ | 4-$CH_3OC_6H_4$ | $CF_3$ | $CF_3$ | $CH_3$ | H | (−27% @ 50)[1,2] |
| 6 | 4-$FC_6H_4$ | 4-$FC_6H_4$ | $CF_3$ | $CF_3$ | $CH_3$ | H | 3.4 |
| 7 | 4-$CH_3C_6H_4$ | 4-$CH_3C_6H_4$ | $CF_3$ | $CF_3$ | H | H | 5.4 |
| 8 | 4-$ClC_6H_4$ | 4-$ClC_6H_4$ | $CF_3$ | $CF_3$ | H | H | 7.0 |
| 9 | $C_6H_5$ | $C_6H_5$ | $CF_3$ | $CF_3$ | H | H | 8.0 |

Notes:
[1] Values in parentheses indicate the percent paw volume reduction at the indicated dose.
[2] Although inactive at the dose indicated, this compound is expected to be active at higher doses.

What is claimed is:

1. A compound of the formula

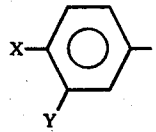

$R_1$ and $R_2$ independently = 2-pyridyl, 3-pyridyl, 4-pyridyl or

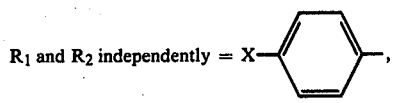

where X=H, F, Cl, Br, $C_1$-$C_2$ alkyl, $C_1$-$C_2$ alkoxy, di($C_1$-$C_2$ alkyl)amino, ($C_1$-$C_2$ alkyl)S(O)$_n$ or $NO_2$; where
n=0, 1 or 2;
Y=H, F or Cl; provided when Y=F or Cl, then X must be F or Cl; further provided that only one of $R_1$ and $R_2$ can be selected from the group of 2-pyridyl and 4-pyridyl;
$R_3$ and $R_4$ independently=H, $CF_3$, $CF_2H$, $CF_2Cl$, $CFCl_2$ or $CF_2CF_3$; provided that no more than one of $R_3$ or $R_4$ is H; and further provided that no more than one of $R_3$ or $R_4$ is $CF_2CF_3$;
$R_5$ and $R_6$ independently=H or $C_1$-$C_3$ alkyl; or a pharmaceutically suitable acid addition salt thereof.

2. A compound of claim 1 wherein $R_1$ and $R_2$ independently = X—⌬—, where X=H, F, Cl, $CH_3O$ or $CH_3$.

3. A compound of claim 1 wherein $R_3$ and $R_4$=trifluoromethyl.

4. A compound of claim 1 wherein $R_5$=H or $CH_3$.

5. A compound of claim 1 wherein $R_6$=H.

6. A compound of claim 1 wherein
$R_1$ and $R_2$ independently=4—$XC_6H_4$—, where X=H, F, Cl, $CH_3O$ or $CH_3$;
$R_3$ and $R_4$=trifluoromethyl;
$R_5$=H or $CH_3$; and
$R_6$=H.

7. The compound of claim 1 which is 4,5-bis(4-methoxyphenyl)-α,α-di(trifluoromethyl)-1H-imidazole-2-methanamine.

8. The compound of claim 1 which is 4,5-bis(4-fluorophenyl)-α,α-di(trifluoromethyl)-1H-imidazole-2-methanamine.

9. The compound of claim 1 which is 4,5-bis(4-fluorophenyl)-1-methyl-α,α-di(trifluoromethyl)-1H-imidazole-2-methanamine.

10. A pharmaceutical composition for the treatment of inflammation consisting essentially of a suitable pharmaceutical carrier and an effective antiinflammatory amount of a compound of claim 1.

11. A pharmaceutical composition for the treatment of inflammation consisting essentially of a suitable pharmaceutical carrier and an effective antiinflammatory amount of a compound of claim 2.

12. A pharmaceutical composition for the treatment of inflammation consisting essentially of a suitable pharmaceutical carrier and an effective antiinflammatory amount of a compound of claim 3.

13. A pharmaceutical composition for the treatment of inflammation consisting essentially of a suitable pharmaceutical carrier and an effective antiinflammatory amount of a compound of claim 4.

14. A pharmaceutical composition for the treatment of inflammation consisting essentially of a suitable pharmaceutical carrier and an effective antiinflammatory amount of a compound of claim 5.

15. A pharmaceutical composition for the treatment of inflammation consisting essentially of a suitable pharmaceutical carrier and an effective antiinflammatory amount of a compound of claim 6.

16. A pharmaceutical composition for the treatment of inflammation consisting essentially of a suitable pharmaceutical carrier and an effective antiinflammatory amount of the compound of claim 7.

17. A pharmaceutical composition for the treatment of inflammation consisting essentially of a suitable pharmaceutical carrier and an effective antiinflammatory amount of the compound of claim 8.

18. A pharmaceutical composition for the treatment of inflammation consisting essentially of a suitable pharmaceutical carrier and an effective antiinflammatory amount of the compound of claim 9.

19. A method for treatment of inflammation in a mammal which comprises administering to the mammal an antiinflammatory amount of a compound of claim 1.

20. A method for treatment of inflammation in a mammal which comprises administering to the mammal an antiinflammatory amount of a compound of claim 2.

21. A method for treatment of inflammation in a mammal which comprises administering to the mammal an antiinflammatory amount of a compound of claim 3.

22. A method for treatment of inflammation in a mammal which comprises administering to the mammal an antiinflammatory amount of a compound of claim 4.

23. A method for treatment of inflammation in a mammal which comprises administering to the mammal an antiinflammatory amount of a compound of claim 5.

24. A method for treatment of inflammation in a mammal which comprises administering to the mammal an antiinflammatory amount of a compound of claim 6.

25. A method for treatment of inflammation in a mammal which comprises administering to the mammal an antiinflammatory amount of the compound of claim 7.

26. A method for treatment of inflammation in a mammal which comprises administering to the mammal an antiinflammatory amount of the compound of claim 8.

27. A method for treatment of inflammation in a mammal which comprises administering to the mammal an antiinflammatory amount of the compound of claim 9.

* * * * *